United States Patent [19]
Kobashi et al.

[11] Patent Number: 5,593,893
[45] Date of Patent: Jan. 14, 1997

[54] DISPENSING DEVICE WITH SYRINGE DRIVING COMPENSATOR FOR FLEXIBLE TUBE

[75] Inventors: Masayuki Kobashi; Noriaki Koeda; Yoshiteru Mizuno, all of Kobe; Satoru Okada, Akashi, all of Japan

[73] Assignee: TOA Medical Electronics Co., Ltd, Hyogo-ken, Japan

[21] Appl. No.: 404,604

[22] Filed: Mar. 15, 1995

[30]  Foreign Application Priority Data

Mar. 15, 1994 [JP] Japan .................................. 6-044394

[51] Int. Cl.$^6$ .................................................. G01N 35/10
[52] U.S. Cl. .................. 436/50; 422/67; 422/81; 422/100; 422/116; 436/49; 436/54; 436/55; 436/180; 73/864.11; 222/52; 222/63; 134/88; 134/22.11
[58] Field of Search ................................ 422/100, 63, 67, 422/81, 116; 436/43, 49, 50, 54, 180, 55; 73/864.01, 864.11, 864.13, 864.22, 864.24, 864.15, 864.16; 134/88; 222/52, 63, 108, 109, 214

[56]  References Cited

U.S. PATENT DOCUMENTS

| 4,457,184 | 7/1984 | Shiono ................................. 73/864.11 |
| 4,459,267 | 7/1984 | Bunce et al. ............................. 422/100 |
| 4,586,546 | 5/1986 | Mezei et al. ................................. 141/2 |
| 4,926,701 | 5/1990 | Tompkins .............................. 73/864.15 |
| 5,133,373 | 7/1992 | Hoffman et al. .......................... 134/88 |
| 5,186,194 | 2/1993 | Kitajima ................................... 134/154 |
| 5,216,926 | 6/1993 | Lipscomb ............................. 73/864.25 |

FOREIGN PATENT DOCUMENTS

| 4-274764 | 9/1992 | Japan . |
| 6-34497  | 2/1994 | Japan . |
| 6-27121  | 2/1994 | Japan . |

*Primary Examiner*—Long V. Le

[57]  ABSTRACT

A dispensing device having a flexible tube provided with a pipetting nozzle at an end, a washing solution supplier supplying washing solution to the flexible tube and the pipetting nozzle, a syringe connected to another end of the flexible tube and a control section for controlling the driving of the syringe. The control section of the present invention includes a syringe driving compensator by which the washing solution is supplied into or discharged out of the syringe in an amount compensate for the variation in the inner volume of the tube caused by reduction in the liquid pressure when the washing solution is transmitted from the washing solution supplier into the flexible tube. The liquid surface of the washing solution contained in the pipetting nozzle is maintained at a constant level by actuating the driving compensator in response to the completion of washing of the pipetting nozzle with the washing solution.

8 Claims, 5 Drawing Sheets

DISPENSING DEVICE WITH SYRINGE DRIVING COMPENSATOR FOR FLEXIBLE TUBE

BACKGROUND OF THE INVENTION

1. Field of the Invention

The invention relates to a dispensing device. In particular, it relates to a dispensing device capable of determining a trace mount of a sample, i.e., sucking or dispensing the sample, which comprises a flexible tube provided with a pipetting nozzle at an end thereof, a washing solution supplier supplying a washing solution to the flexible tube and the pipetting nozzle, a syringe connected to another end of the flexible tube and a control section for controlling the driving of the washing solution supplier and the syringe.

2. Description of the Related Art

A conventional dispensing device is mainly composed of a tube provided with a pipetting nozzle at an end and a syringe connected to another end of the tube, which enables a sample or a washing solution to be sucked or discharged through a pipetting nozzle by actuating a piston in the syringe.

Some dispensing devices comprising a washing solution supplier for washing the pipetting nozzle, tube and syringe through which the sample passes wash the pipetting nozzle by supplying a pressed washing solution from the syringe side to the pipetting nozzle via the flexible tube or from the pipetting nozzle to the syringe via the flexible tube.

In addition, the following prior arts are known. Japanese Laid-open Patent Publication No. Hei 4 (1992)-274764 discloses a structure wherein the pressure in a tube is detected by a sensor when moving a pipetting nozzle to a predetermined place after finishing suction for measurement and the pressure in the tube is maintained at a certain level by actuating the syringe for suction to prevent a sample liquid from dropping out from the tip of the pipetting nozzle.

Japanese Laid-open Patent Publication No. Hei 6 (1994)-27121 describes a syringe works for suction that cuts the liquid drop on the tip of the nozzle after discharging the liquid. Further, Japanese Laid-open Patent Publication No. Hei 6 (1994)-34497 describes a syringe that comprises a pipe provided with a suction valve and an ejecting valve, and a syringe works for suction that cuts off the liquid drop on the tip of the nozzle after discharging the liquid.

The conventional dispensing device may be used for an automatic analyzer such as an automated immunochemical analyzer, in which the pipetting nozzle is inserted in a sample container and the syringe starts sucking a predetermined mount of the sample through the flexible tube. Then, the pipetting nozzle is transmitted to a reaction container. When the pipetting nozzle is inserted in the reaction container, the syringe starts discharging the predetermined amount of the sample sucked in the flexible tube or syringe.

Subsequently, the pipetting nozzle is washed by the washing solution supplier. In this process, the washing solution or air for washing the pipetting nozzle was strongly discharged from the syringe side to the tip of the pipetting nozzle or, on the contrary, strongly sucked from the tip of the pipetting nozzle to the syringe side, thereby cleanly washing contamination inside of the pipetting nozzle caused by sample pipetting. Then, the pipetting nozzle is transmitted between the sample container and the reaction container relatively to enter another sucking/dispensing process.

The dispensing device disclosed in Japanese Laid-open Patent Publication No. Hei 4 (1992)-274764 has defects in the delay of response and the easy generation of uneven sensitivity because feedback control is conducted based on the pressure data in the tube detected by the sensor. It is hard to determine at a high speed and with good accuracy.

According to the dispensing devices disclosed in Japanese Laid-open Patent Publication Nos. Hei 6 (1994)-27121 and Hei 6 (1994)-34497, the liquid drop on the tip of the pipetting nozzle can be cut off. However, these devices do not solve the problems of the delay of determination time and of the deterioration of accuracy owing to the expansion and contraction of the tube connected to the nozzle and syringe.

Figure 8:
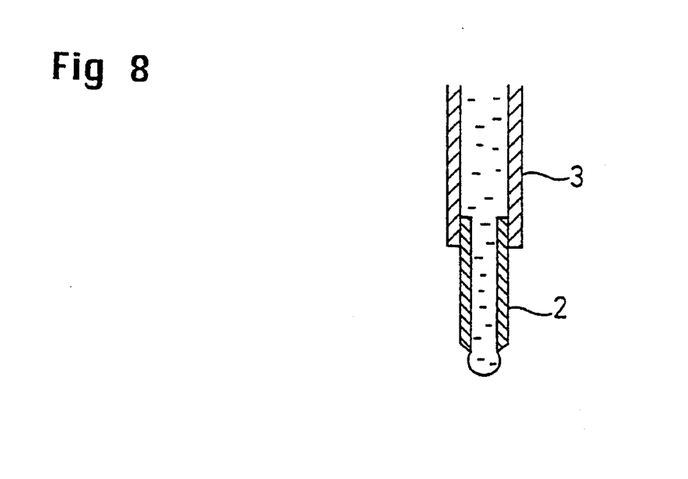
FIG. 8 is a schematic sectional view corresponding to FIG. 5 showing a pipetting nozzle and washing solution in a tube which is restored after the conventional washing process.

When the washing solution is supplied from the syringe side of the dispensing device in the washing process, pressure is applied to the inside of the tube and the tube is expanded (see FIG. 6), whereby the inner volume of the flexible tube 3 is increased. The expanded tube 3 regains the initial shape for several seconds after washing. The gradual restoration of the expanded tube leads the washing solution which remains in the tube 3 to the tip of the pipetting nozzle 2 as the liquid drop (the liquid drop shown in FIG. 8).

Figure 7:
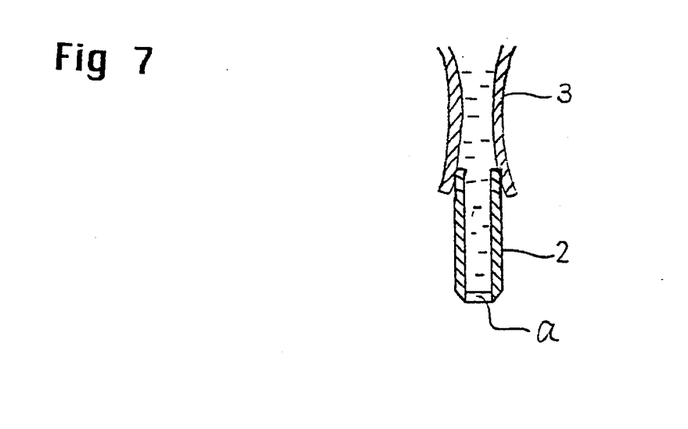
FIG. 7 is a schematic sectional view of the second embodiment of the present invention showing a tube and washing solution soon after the washing process is completed.

When the washing solution is sucked from the tip of the pipetting nozzle 2 in the washing process, the tube 3 is contracted (see FIG. 7). The contracted tube 3 gradually regains the initial shape by its own restoration force. However, the pressure inside of the tube 3 is reduced because of the restoration, so that the washing solution is sucked into the pipetting nozzle 2.

The tube 3 deformed in the washing process induces determination errors of the sample, which causes a significant problem in determining a trace amount of sample such as a several micron liters.

Generally, the mount of the water solution used in the washing process ranges from several times to several thousand times the amount of the liquid sample. It may take 10 seconds or more for the expanded or contracted tube deformed by discharging or sucking such a great amount of washing solution to regain its initial shape and allow another pipetting action of a trace amount of the sample. The time causes a delay in the measurement.

On the other hand, if the flexible tube described above is not used, it would be difficult to move the pipetting nozzle between a plurality of reaction containers up and down or rotationally (relative transmittance).

SUMMARY OF THE INVENTION

The present invention provides a dispensing device comprising a flexible tube provided with a pipetting nozzle at an end thereof, a washing solution supplier for supplying a washing solution to the flexible tube and the pipetting nozzle, a syringe connected to another end of the flexible tube and a control section for controlling the driving of the syringe, wherein the control section includes a syringe driving compensator by which the washing solution is supplied into or discharged out of the syringe in an amount to compensate for the variation in the inner volume of the tube caused by the reduction in the liquid pressure when the washing solution is transmitted from the washing solution supplier into the flexible tube, and the liquid surface of the washing solution contained in the pipetting nozzle is maintained at a constant level by activating the driving compensator after the pipetting nozzle has been washed with the washing solution.

DETAILED DESCRIPTION OF THE INVENTION

The dispensing device of the present invention:

is capable of pipetting with a high accuracy at a rapid speed;

can control the delay in response and uneven sensitivity caused by the control of the syringe driving means used for sample pipetting;

can prevent generating a liquid drop on the tip of the pipetting nozzle;

is capable of washing the flexible tube and pipetting nozzle after pipetting the sample and which does not generate inaccuracies when determining a sample caused by remaining washing solution;

is capable of determining a sample by relatively transmitting the pipetting nozzle between a plurality of reaction containers by using a flexible tube;

does not generate inaccuracies when determining a sample which are caused by the deformation of the flexible tube by pressure applied by the washing solution and/or is capable of pipetting a sample by using the flexible tube while it is being restored to its natural shape without waiting for its restoration.

The flexible tube of the present invention has an inner diameter e.g., 1.2 mm, an outer diameter e.g., 2.5 mm, and a length e.g., 1500 mm. The material of the tube is not specifically limited but may be made of polyurethane resin, silicon resin, Teflon resin or polyethylene resin.

The pipetting nozzle of the present invention is preferably formed of a fine tube capable of pipetting a trace amount of sample.

The syringe of the present invention may be those having a piston moving up and down or rotationally in the cylinder.

The water solution supplier of the present invention comprises a water solution supplying passage through which a washing solution is supplied to the syringe through a washing solution conduit via a valve and is discharged from the pipetting nozzle, or through which the washing solution is supplied from a washing solution storing tank through the pipetting nozzle to the syringe and is discharged from the washing solution conduit. The washing solution supplier of the present invention may be controlled by the same control section as that for to the syringe driving means, or may be controlled by another control means installed outside. The control section may include the syringe driving compensator and a functional signal generator.

The control section of the present invention should preferably control the driving of the syringe such that the liquid is sucked and discharged accurately with a sufficient resolving power (sufficient to cancel the deformed content of the tube). Further, the control section should preferably control the action of the valve and the pump for supplying the washing solution in the washing solution supplier.

Compensation for the variation in the inner volume of the tube of the present invention means to compensate for the amount of increased volume caused by the liquid pressure generated by discharging the washing solution from the pipetting nozzle after supplying it in the syringe via the conduit. Compensation for the variation also means to compensate for the amount of volume decreased by reduction in the pressure of the tube caused by the suction of the washing solution into the syringe through the pipetting nozzle from the washing solution storing tank. In the former case, the generation of a liquid drop caused by the restoration of the tube is prevented, while in the latter case, an excessive uptake of sample in the pipetting process is prevented. The compensation leads to a rapid transmittance of the sample for the next pipetting process and leads to an accurate determination. Since the variation in the inner volume of the tube depends on the material or size (inner diameter, outer diameter and length) of the tube, compensation is necessary in accordance with the variation.

The syringe driving compensator of the present invention controls the syringe driving means such that the variation in the inner volume caused by the restoration of the tube is compensated for.

The syringe driving compensator preferably actuates the syringe such that the liquid surface of the washing solution contained in the pipetting nozzle is maintained at a constant level while the reduction in tube volume due to the suction of washing solution through the pipetting nozzle is returned to normal. For example, a preferred syringe driving compensator is provided with a pulse motor which allows a piston in the syringe to move within a small range.

The syringe driving compensator also preferably actuates the syringe such that the liquid surface of the washing solution contained in a pipetting nozzle is maintained at a constant level while the increase in tube volume caused by the discharge of washing solution through the pipetting nozzle is returned to normal. For example, a preferred syringe driving compensator is cooperated with the function signal generator outputting a driving signal which corresponds the time function with the restoration of the deformed tube.

The function signal generator gives a pulse signal to the syringe driving compensator connected to the syringe driver such as the pulse motor to compensate with a driving amount. The driving amount may be smaller than that of the pipetting syringe. Preferably, the function signal generator can control the driving by using the syringe driving compensator in accordance with the predetermined timing for starting and finishing syringe movement per time.

The control section of the present invention gives an instruction to the syringe to drive it for sucking and discharging the sample.

Provided that the process starts from sucking the sample, the pipetting nozzle is inserted into the sample container and the syringe starts to suck a certain amount of the sample through the flexible tube.

In the process of discharging, the pipetting nozzle is moved to the reaction container and inserted therein. The syringe starts discharging the determined sample to the reaction container through the flexible tube.

As described above, the pipetting nozzle can be moved relatively between a plurality of reaction containers by using a flexible tube.

When the washing solution is discharged out of the pipetting nozzle, the pipetting nozzle is moved to the washing tank after discharging the sample and inserted therein. The washing solution supplied from the washing solution supplier is discharged through the syringe and the flexible tube, so that contamination in the pipetting nozzle is cleaned. In this process, the flexible tube is expanded by the washing solution supplied from the pipetting nozzle from the syringe side.

The expanded flexible tube gradually regains its initial shape by its own restoration power. In restoring, the syringe is driven by the driving compensator which is instructed by the control section simultaneous with the completion of washing of the pipetting nozzle with the washing solution such that the washing solution is supplied into the syringe in an mount to compensate the variation of inner volume during the restoration of the tube expanded by the liquid pressure, and the liquid surface of the washing solution contained in the pipetting nozzle is maintained at a constant level. In this process, the washing solution is prevented from being projected or dropped out from the tip of the pipetting nozzle. Accordingly, a certain volume of air which is formed on the liquid surface of the tip of the washing solution in the pipetting nozzle intervenes between the sample and the washing solution, thereby preventing the washing solution and the sample from being mixed with each other.

Alternatively, when the washing solution is sucked from the pipetting nozzle, the pipetting nozzle is moved to the washing tank and inserted therein. The washing solution supplied from the washing solution supplier is sucked from the syringe side (on the contrary to the above) and discharged through the flexible tube to the syringe side, so that contamination in the pipetting nozzle is cleaned. In this process, the flexible tube is contracted by sucking from the syringe side, i.e., supplying the washing solution from the pipetting nozzle to the syringe side.

The flexible tube contracted by the reduced pressure gradually regains its initial shape. During the restoration, the syringe is driven by the driving compensator which is instructed by the control section in response to the completion of washing of the pipetting nozzle with the washing solution such that the washing solution is supplied into the syringe in an amount to compensate for the variation of inner volume during the restoration of the tube contracted by the reduced pressure. Accordingly, the reduced pressure in the tube is canceled before starting next pipetting process, thereby preventing an excessive suction of the sample in the pipetting process. As a result, the liquid surface of the washing solution contained in the pipetting nozzle is maintained at a constant level.

The syringe driving compensator is cooperated with the function signal generator which is used for outputting a driving signal which corresponds to the time function for the restoration of the deformed tube in order to control the predetermined amount of syringe movement per unit of time.

As described above, since the compensation can be performed on the basis of the predetermined chart, there is no delay in response. In addition, as a pressure sensor is not used, the device does not suffer from the uneven sensitivity caused by the sensor.

Further, the liquid surface is maintained at a constant level, whereby the sample can be determined soon after the first determination without waiting for restoration of the flexible tube. Therefore, the determination can be performed with high accuracy at a high speed, which is especially effective in determining a trace amount of sample such as several micro-liters in a predetermined time.

According to the dispensing device of the present invention, the liquid surface of the washing solution contained in the pipetting nozzle is maintained at a constant level irrespective of the time elapsed after the completion of the washing by driving the syringe driving compensator. Accordingly, a certain volume of air which is formed on the liquid surface of the tip of the washing solution in the pipetting nozzle intervenes between the sample and the washing solution, thereby preventing the washing solution and the sample from being mixed with each other.

Even when the flexible tube is expanded by dispensing the washing solution out of the pipetting nozzle to wash the tube, the washing solution is prevented from being projected or dropped out from the tip of the pipetting nozzle.

Alternatively, when the flexible tube is contracted by sucking the washing solution from the syringe side, the reduced pressure in the tube is canceled before starting next pipetting process, thereby preventing an excessive suction of the sample in the pipetting process.

Accordingly, next pipetting can be performed without waiting for natural restoration of the deformed tube.

Since the syringe driving compensator is cooperated with the function signal generator, precise control of the compensation of the syringe can be performed. The liquid surface of the washing solution contained in the pipetting nozzle is maintained at a certain level with high accuracy. As a result, the present invention can provide the dispensing device of which accuracy in determining does not deteriorate by the deformed tube caused by the liquid pressure of the washing solution.

According to the dispensing device of the present invention, the pipetting nozzle can be transmitted between a plurality of reaction containers by using a flexible tube, so that the determination can be made efficient.

According to the dispensing device of the present invention, a dispensing device capable of washing the flexible tube and pipetting nozzle after pipetting the sample and which does not generate inaccuracies when determining a sample caused by remaining washing solution can be provided.

The generation of a liquid drop on the tip of the pipetting nozzle can be also prevented by the present invention.

Since the compensation can be performed on the basis of the chart in which the compensation of the driving is predetermined, there is no delay in response when controlling the syringe driving. In addition, as a pressure sensor is not used, the device does nor suffer from the uneven sensitivity caused by the sensor.

As described above, the liquid surface is maintained at a constant level, whereby the sample can be determined with high accuracy irrespective of waiting time for the next pipetting. The feature is especially effective in determining a trace amount of sample such as several microns liters.

Further, it is possible to enter the next pipetting process immediately without waiting for the restoration of the deformed tube. Therefore, the rapid determining is made possible by the present invention. The feature is especially effective in determining a trace amount of sample such as several micro-liters in a predetermined time.

As described above, according to the present invention, a dispensing device capable of determining the sample with high accuracy at a high speed can be provided.

EXAMPLE 1

Figure 1:
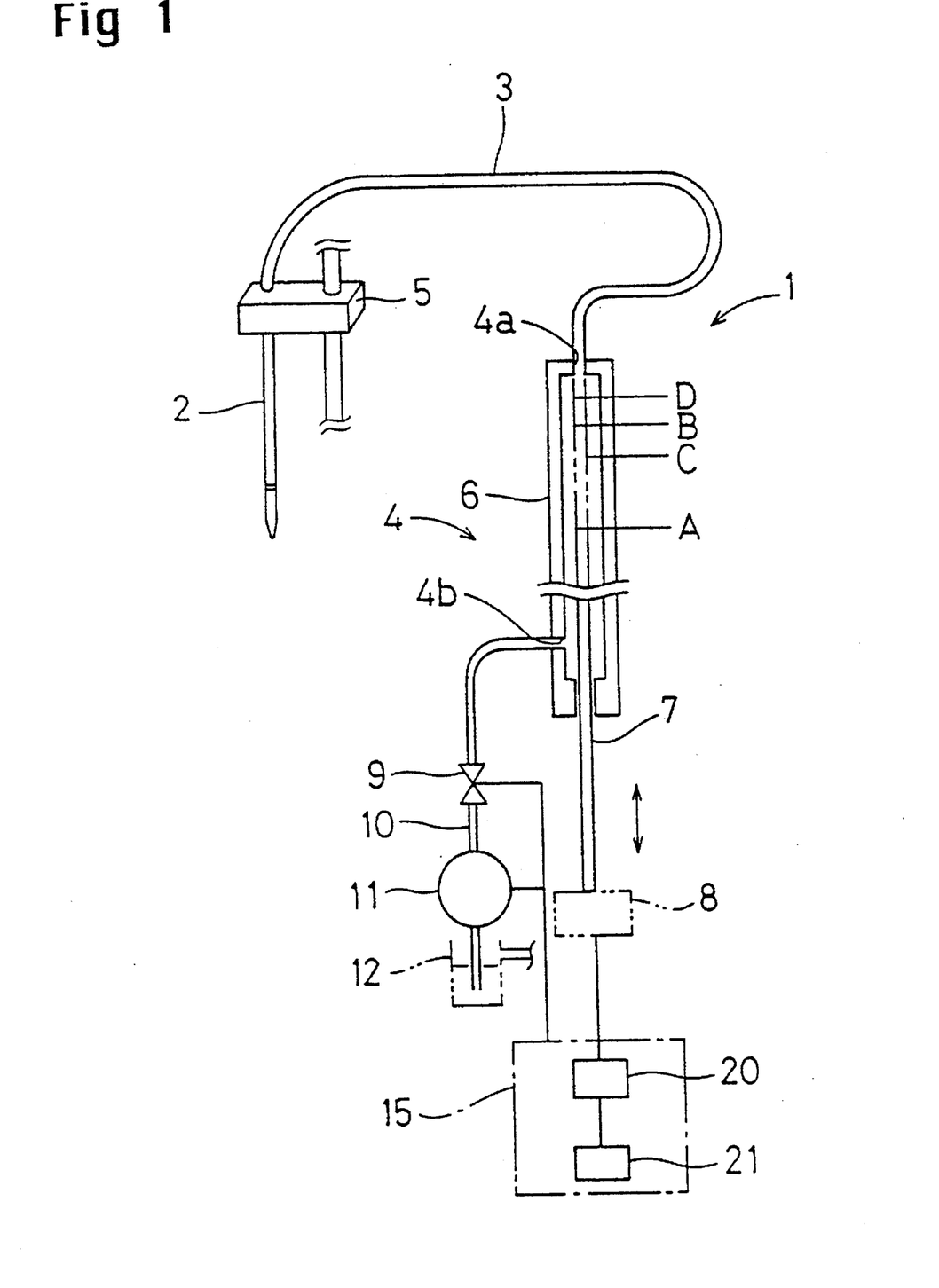
FIG. 1 is a schematic diagram showing a dispensing device of an example of the present invention.

FIG. 1 shows a dispensing device of an example of the present invention.

A dispensing device 1 mainly comprises a pipetting nozzle 2, a tube 3 connected to the upper end of the nozzle 2 and a syringe 4. The pipetting nozzle 2 is secured to a supporting arm 5 which is movable in three axis direction by a driving means (not shown). The pipetting nozzle 2 has a tapered opening at the bottom. The tube 3 is connected to the pipetting nozzle 2 at the other side of the tapered end of the pipetting nozzle 2, and connected to the syringe 4 at an end which is not connected to the pipetting nozzle 2.

The tube 3 is made of materials which does not cause deterioration such as corrosion and swelling to a sample solution. A preferred material is polyurethane. Preferably, the tube 3 is flexible and has an inner diameter of 1.2 mm and an outer diameter of 2.5 mm. The length of the tube 3 may be about 1.5 m. The tube 3 is kept such that the pipetting nozzle 2 is not stretched between the pipetting nozzle 2 and the syringe 4 when the pipetting nozzle 2 is moved by the supporting arm 5.

The syringe 4 mainly comprises a cylinder 6, a piston 7 which is slidable in the cylinder 6 and a syringe driver 8 which actuates the piston 7 up and down in the cylinder 6. The cylinder 6 has a capacity of 1000 µl. The outer diameter of the piston 7 is 1 mm.

The piston 7 can be moved straight up and down within a length of about 150 mm at a resolution of about ½₀ mm by means of the driver 8 based on the instruction given by a control section (not shown). About 100 µl of liquid can be carried by one stroke of the piston 7.

A connecting opening 4a to which one end of the tube 3 is connected is formed on the upper portion of the cylinder 6, and a connecting opening 4b is formed on the lower side surface of the cylinder 6 for supplying washing solution. The connecting opening 4b, which works as an inlet, is connected to a conduit 10 for washing solution having a magnetic valve 9. On the other end of the conduit 10 for washing solution, a pump 11 is connected, thereby forming a washing solution supplier to supply the washing solution between the syringe 4 and the pipetting nozzle 2.

The syringe driver 8 is provided with a pulse motor having a ball screw. The pulse motor transmits a rotational power to the piston 7 through the ball screw to move the piston 7 up and down. The syringe driver 8 is connected to a control section 15 which controls the driving of the syringe used for pipetting and also controls the driving of the syringe to compensate for the deformed tube by a syringe driving compensator 20 which is provided in the control section 15. A function signal generator 21 capable of outputting a driving signal corresponding m the restoration of the tube 3 is connected to the syringe driving compensator 20.

Figure 2:
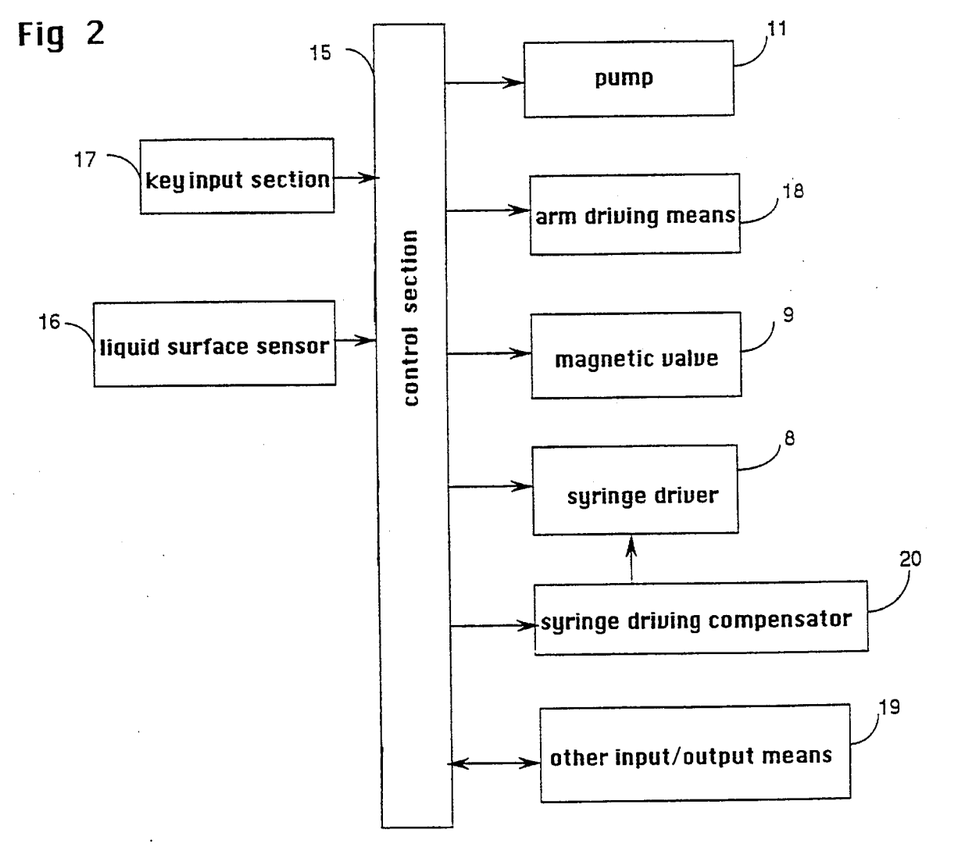
FIG. 2 is a schematic block chart showing the dispensing device of FIG. 1.

The supporting arm 5 works for fixing the pipetting nozzle 2. A liquid surface sensor (not shown) is installed in the supporting arm 5 in order to detect the surface of liquid contained in a sample container to which the pipetting nozzle 2 is inserted. The driving mechanism which includes the syringe driver 8, magnetic valve 9 and supporting arm 5 and the liquid surface sensor are electrically connected to the control section 15. FIG. 2 shows a block chart of the dispensing device 1.

The dispensing device 1 includes the control section 15 having a microcomputer comprising CPU, ROM, RAM, timer, counter and the like. Connected to the control section 15 is a liquid surface sensor 16 and a key input section 17 which is not shown. Further, the pump 11, magnetic valve 9, an output means such as the syringe driver 8 and an arm driving means 18, and other input/output means 19 are also connected to the control section 15.

The action of the dispensing device 1 of this Example is described hereinafter.

First, the bottom end of the pipetting nozzle 2 is inserted in the sample container (not shown). Then, a driving signal of 100 to 200 pulse is sent to the pulse motor 8a from the control section to actuate the syringe 4 for sucking a desired amount, for example 20 µl, of the sample solution contained in the sample container through the tube 3 (a process of sucking the sample). The reference letter A in FIG. 1 shows a position of the piston 7 in the cylinder after suction.

Next, the pipetting nozzle 2 is moved onto the reaction container and the bottom end of the pipetting nozzle 2 is inserted into the reaction container. A driving signal of 100 to 200 pulse is sent from the control section 15 to the pulse motor 8a to move the syringe 4 for discharging the sample (a process of discharging the sample). The reference letter B in FIG. 1 shows a position of the piston 7 in the cylinder 6 after discharging.

Figure 3:
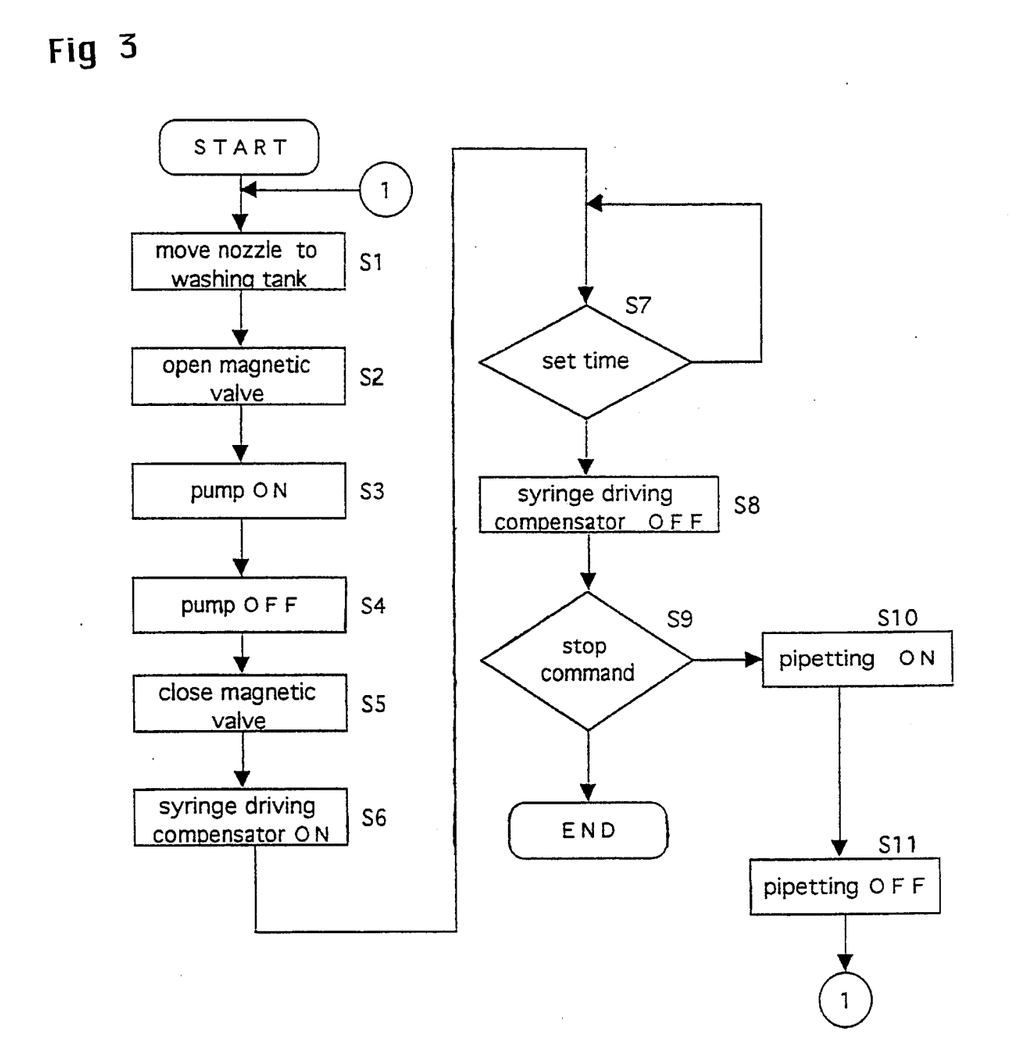
FIG. 3 is a control flow chart of the dispensing device of FIG. 1.

The action from the washing process is described with reference to the control flow chart in FIG. 3. In step S1, the pipetting nozzle 2 is moved onto the washing tank by the arm driver and the tip of the pipetting nozzle 2 is inserted into the tank. The depth to which the pipetting nozzle 2 is inserted in the tank is controlled by the liquid surface sensor 16. The magnetic valve 9 is opened in step S2. The pump 11 is driven to carry the washing solution in the washing solution storing tank 12 through the washing solution conduit 10 to the syringe 4 side in step S3. The washing solution is charged from the connecting opening 4b to the cylinder 6 for about 4 seconds and discharged from the pipetting nozzle 2.

Then, the driving of the pump is stopped in step S4. While compensating the driving before stopping, about 2 ml of the washing solution is supplied for a total of 4 seconds at a pressure of 0.4 kg/cm². The magnetic valve 9 is closed in step S5 to finish washing.

Figure 6:
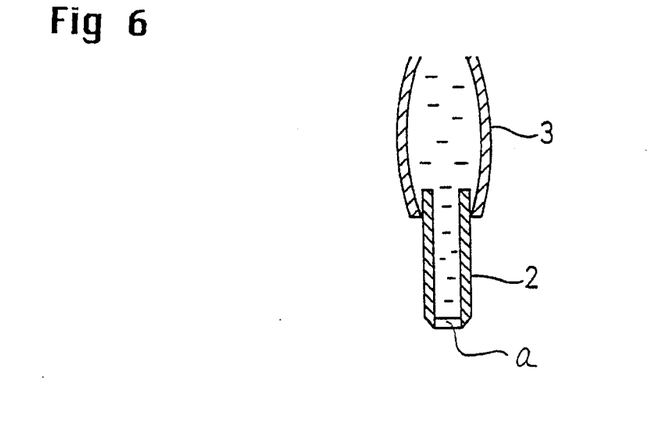
FIG. 6 is a schematic sectional view of the first embodiment of the present invention showing a tube and washing solution soon after the washing process is completed.

When the contamination in the pipetting nozzle 2 is cleaned by washing, the tube 3 is slightly expanded by the pressure of the washing solution as shown in FIG. 6 and an excessive amount of water which corresponds to the amount of expansion of the tube 3 remains in the tube 3. As shown in FIG. 6, an air layer a having a small thickness is formed on the tip of the pipetting nozzle 2. The air layer a works to separate the sample from the washing solution in the pipetting nozzle 2. The expanded tube 3 gradually regains its initial shape by its own elasticity.

Next, a driving signal is sent to the pulse motor 8a in step S6 to compensate for the amount of expansion. Namely, based on the graph showing a relationship between the mount necessary for compensation and the time elapsed after completion of washing in FIG. 4, the function signal generator 21 generates a pulse signal which is a time function along the line y and the piston 7 is gradually moved from the position B to the lower at a constant speed by sending a pulse signal of 7 to 8 pulse to the pulse motor 8a, whereby the washing solution in the expanded tube is sucked into the syringe 4.

Figure 4:
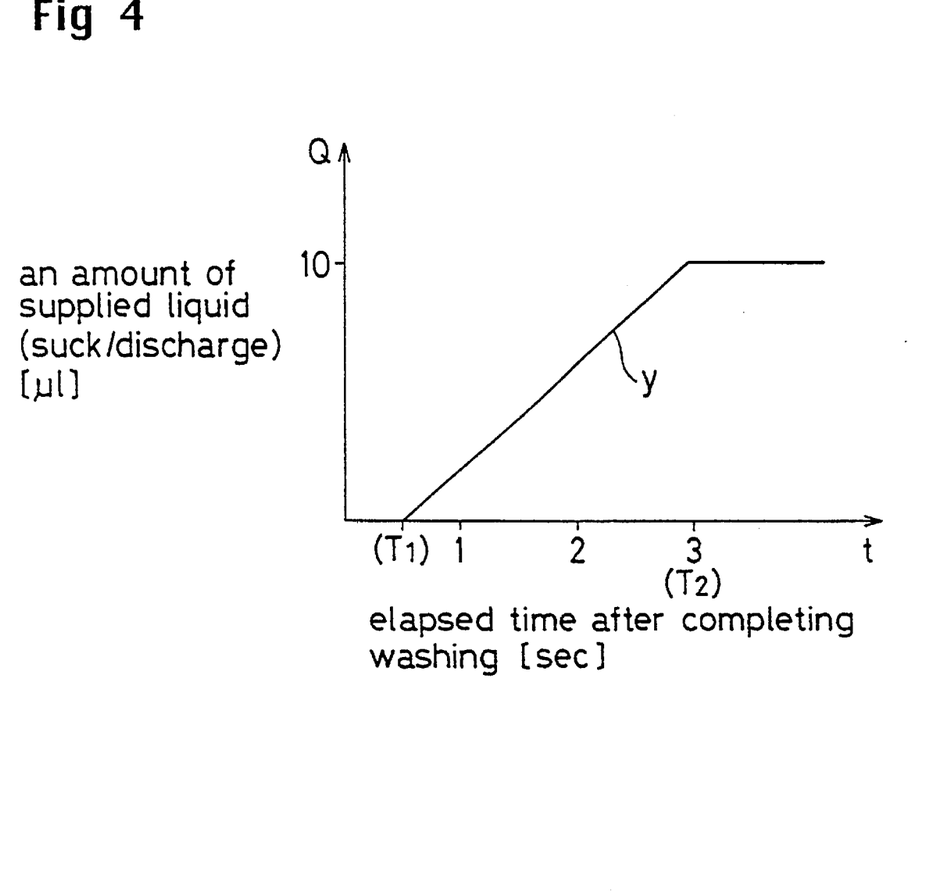
FIG. 4 is a graph showing a syringe driving compensator after washing has been completed.

Accordingly, about 10 µl of the washing solution is sucked in about 3 seconds and the piston 7 is moved to the position C. More precisely, the suction starts 0.5 seconds after completing the discharge of washing solution and the washing solution is sucked continuously at 4.1 µl /sec.

Figure 5:
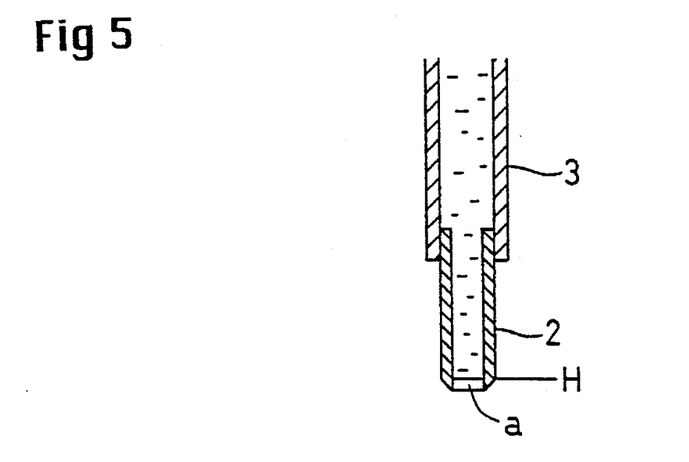
FIG. 5 is a schematic sectional view showing a pipetting nozzle which is controlled by syringe driving means after the washing process is completed and showing washing solution in a tube.

When 3 seconds elapses in step S7, the driving is stopped in step S8 and the excessive washing solution in the tube 3 is sent back to the cylinder 6. As a result, the position H which is the surface of the washing solution in the pipetting nozzle 2 is maintained irrespective of the time elapsed after washing (see FIG. 5). Accordingly, while the expanded tube 3 is contracted to regain the initial shape, the excessive washing solution which remains in the tube 3 is not pushed out from the pipetting nozzle 2 and the air layer a with a constant volume is formed on the tip of the pipetting nozzle 2.

In step S9, it is decided whether to stop the driving. When it is decided that driving should not stop, proceed to step S10. Once the pipetting starts in step S10, the sample sucked from the top of the pipetting nozzle 2 comes into contact with the washing solution in the pipetting nozzle 2 through the air layer a having a constant volume, which prevents mixing of the sample and the washing solution with certainty. When the driving of the syringe is stopped in step S11 and the pipetting is finished, the procedure comes back to step S1 to initiate the washing described above. When it is decided that the process should stop at step S9, the process is finished without proceeding to the pipetting process.

In this example, the suction of the syringe 4 is performed until the tube 3 regains its initial shape, while the liquid surface is maintained at a certain level. Accordingly, there is no need to wait until the tube 3 is restored by its own elasticity. As a result, even while the tube 3 is in restoration, another sample can be taken with good accuracy.

EXAMPLE 2

Example 2 is conducted in the same manner except that the washing solution storing tank 12 is disposed in the lower position of the pipetting nozzle 2 which is moved relatively and the washing tank is disposed at a place where the washing solution storing tank 12 is positioned because the pump 11 is used for sucking the washing solution when washing.

The action different from the Example 1 is now described with reference to the control flow chart in FIG. 3 after the process of discharging of the sample. In step S1, the pipetting nozzle 2 is moved to the washing tank by the arm driver and the tip of the pipetting nozzle 2 is inserted into the washing tank. The pipetting nozzle 2 stops going down in the washing solution storing tank 12. Next, the magnetic valve 9 is opened in step S2, and the washing solution in the washing solution storing tank 12 is carried through the pipetting nozzle 2 by driving the pump 11 to the syringe 4 side and is discharged through the washing solution conduit 10 to the washing tank connected to the pump 11.

The driving of the pump 11 is stopped in step S11, in which about 2 ml of the washing solution in total is sucked for 4 seconds at –300 mmHg. Then, the magnetic valve 9 is closed in step S9.

When the contamination in the pipetting nozzle 2 is cleaned in the washing process described above, the tube 3 is slightly contracted by driving the pump 11 as shown in FIG. 7. The flexible tube 3 contracted by the reduced pressure gradually starts restoration.

Next, a driving signal is sent to the pulse motor 8a in step S6 to start sucking for compensation. Namely, based on the graph showing a relationship between the mount necessary for compensation and the time elapsed after completion of the washing in FIG. 4, the function signal generator 21 generates a pulse signal which is a time function along the line y. The piston 7 is gradually moved from the position B to the upper at a constant speed by sending a pulse signal of 7 to 8 pulse to the pulse motor 8a, whereby the washing solution in the syringe 4 is discharged into the contracted tube 3.

The total discharged amount of the washing solution supplied to the pipetting nozzle 2 through the contracted tube 3 in accordance of time is the same as FIG. 4. About 10 µl of the washing solution is sucked in about 3 seconds and the piston 7 is moved to the position D. More precisely, the discharge starts 0.5 seconds after completing the suction of the washing solution and the washing solution is discharged continuously at 4 µl/sec. The suction of the syringe continues until the tube 3 regains the initial shape, while maintaining the liquid surface of the washing solution in the pipetting nozzle 2 at a constant level. In this process, the air layer a having a constant thickness is always formed on the tip of the pipetting nozzle 2 as shown in FIG. 7.

After the steps S7 to S9, pipetting of the sample starts in the same manner as in step S10. The sample to be sucked is separated from the tip of the pipetting nozzle 2 through the intermediary of the air layer a, thereby preventing the sample and the washing solution from being mixed with each other.

According to the setting chart for the compensation driving of the syringe in Examples 1 and 2 described above, the surface of the washing solution in the pipetting nozzle 2 is maintained at a constant level such that T1=0.5 seconds, T2=3 seconds and K=4 µl/second, provided that:

$Q=0$, wherein $0 \leq t < T1$ $Q=K(t-T1)$, wherein $T1 \leq t < T2$ $Q=K(T2-T1)$, wherein $T2 \leq t$.

wherein T and t show elapsed rime after completing washing, Q is an amount of the supplied liquid (sucked and discharged) which is used for driving compensation of the syringe and K is an mount of the supplied liquid (sucked and discharged) per unit time.

In this example, the discharge of the syringe driver 8 is performed until the tube 3 regains the initial shape, while the liquid surface is maintained at a constant level. Accordingly, there is no need to wait until the tube 3 is restored by its own elasticity. As a result, even driving time the tube 3 is in restoration, another sample can be conducted with good accuracy.

Although the example discloses a structure of the syringe in which the piston 6 is moved up and down in the cylinder 7 to perform the suction and discharging, the syringe may perform the suction and discharging by a rotational power obtained by a tubing pump and the like.

In addition, the suction and discharging of the syringe 4 may be controlled based on the data of pressure detected in the pipetting nozzle 2 or syringe 4 when the tube 3 is restored, not by the function of time.

What we claim is:

1. A dispensing device comprising:

a flexible tube provided with a pipetting nozzle at an end thereof;

a washing solution supplier supplying a washing solution to the flexible tube and the pipetting nozzle;

a syringe connected to another end of the flexible tube; and a control section for controlling the driving of the syringe, wherein the control section comprises a syringe driving compensator by which the washing solution is supplied into or discharged out of the syringe in an amount to compensate for a variation in an inner volume of the tube caused by a reduction or an increase in liquid pressure which causes a deformation of the flexible tube when the washing solution is transmitted from the washing solution supplier into the flexible tube, and a liquid surface of the washing solution contained in the pipetting nozzle is maintained at a constant level by activating the driving compensator in response to completion of washing of the pipetting nozzle with the washing solution, the syringe driving compensator further including a function signal generator outputting a driving signal corresponding to a time function of restoration of the deformed flexible tube.

2. A dispensing device according to claim 1, wherein the syringe driving compensator allows the syringe to maintain the liquid surface of the washing solution contained in the pipetting nozzle at the constant level by suction in accordance with restoration of the flexible tube expanded by discharging the washing solution supplied from the washing solution supplier through the pipetting nozzle.

3. A dispensing device according to claim 1, wherein the syringe driving compensator allows the syringe to maintain the liquid surface of the washing solution contained in the pipetting nozzle at the constant level by discharging in accordance with restoration of the flexible tube contracted by sucking the washing solution supplied from the washing solution supplier through the pipetting nozzle.

4. A method of operating a dispensing device including a flexible tube having a pipetting nozzle at a first end and a syringe connected at a second end, comprising the steps of:

washing the pipetting nozzle with a washing solution;

compensating for a variation from an initial state of an inner volume of the flexible tube due to a reduction or an increase in liquid pressure which causes deformation of the flexible tube during said washing step, said compensating step including supplying into or discharging out of the syringe an amount of the washing solution sufficient to compensate for the reduction or increase in liquid pressure;

beginning said compensating step in response to completion of said washing step, thereby maintaining a liquid surface of the washing solution in the pipetting nozzle at a constant level;

generating a driving signal which corresponds to a time function for the restoration of the deformed tube; and performing said compensating step in accordance with said driving signal.

5. A method according to claim 4, wherein said compensating step further includes returning an inner volume of the flexible tube to the initial state after the reduction in the inner volume by suction of the washing solution through the pipetting nozzle.

6. A method according to claim 4, wherein said compensating step further includes returning an inner volume of the flexible tube to the initial state by discharging the washing solution through the pipetting nozzle.

7. A method according to claim 4, further comprising sucking in a desired amount of sample solution to the pipetting nozzle during said compensating step.

8. A dispensing device according to claim 1, wherein said control section begins pipetting of a sample solution through said pipetting nozzle during operation of said syringe driving compensator.

* * * * *